United States Patent

Masaki et al.

[11] Patent Number: 5,954,630
[45] Date of Patent: Sep. 21, 1999

[54] FM THETA-INDUCING AUDIBLE SOUND, AND METHOD, DEVICE AND RECORDED MEDIUM TO GENERATE THE SAME

[75] Inventors: Kazumi Masaki, Osaka; Osamu Matsuda, Okayama, both of Japan

[73] Assignee: Ken Hayashibara, Okayama, Japan

[21] Appl. No.: 08/305,834

[22] Filed: Sep. 14, 1994

[30] Foreign Application Priority Data

Sep. 16, 1993 [JP] Japan .................................. 5-252124
Sep. 24, 1993 [JP] Japan .................................. 5-258973
Sep. 24, 1993 [JP] Japan .................................. 5-258993

[51] Int. Cl.[6] .................................................. A61M 21/00
[52] U.S. Cl. .............................................................. 600/28
[58] Field of Search .......................................... 600/26–28

[56] References Cited

U.S. PATENT DOCUMENTS

| 4,141,344 | 2/1979 | Barbara ..................................... 600/28 |
| 4,227,516 | 10/1980 | Meland et al. ............................. 600/28 |
| 4,335,710 | 6/1982 | Williamson ................................ 600/28 |
| 5,123,899 | 6/1992 | Gall . | |

FOREIGN PATENT DOCUMENTS

| 2569348 | 2/1986 | France . | |
| 4003476 | 8/1991 | Germany .................................. 600/28 |
| 61-56653 | 3/1986 | Japan . | |
| 61-131757 | 6/1986 | Japan . | |
| 61-159970 | 7/1986 | Japan . | |
| 2124491 | 2/1984 | United Kingdom ..................... 600/28 |

OTHER PUBLICATIONS

Agu, M. et al., "1/f fluctuation with pleasant human sensation and its application to household appliances." (abstract) Journal of the Institute of Elecetrical Engineers of Japan, vol. 113, No. 1 (Jan. 1993).

Inouye, Tsuyoshi et al. "EEG Characteristics of Frontal Midline Theta Activity." The EEG of Mental Activities pp. 136–148 (1988).

*Primary Examiner*—John P. Lacyk
*Attorney, Agent, or Firm*—Browdy and Neimark

[57] ABSTRACT

An audible sound of modulated wave where a very low-frequency wave of about 20 hertz or lower is superposed on an audio low-frequency wave effectively stimulates Fm theta in human brain waves to improve attention and concentration during mental tasks when auditorily administered. The audible sound is also effective in stimulation of human alpha wave when the very low-frequency wave lies within the range of about 2–10 hertz. Such audible sound is artificially obtainable by generating an electric signal which contains such a modulated wave, and transducing it into audible sound wave.

20 Claims, 8 Drawing Sheets

FM THETA-INDUCING AUDIBLE SOUND, AND METHOD, DEVICE AND RECORDED MEDIUM TO GENERATE THE SAME

BACKGROUND OF THE INVENTION

1. Field of the Invention

This invention relates to an audible sound which is able to induce Fm theta in human brain waves, as well as to a method, device and recorded medium to generate the same.

2. Description of the Prior Art

Potential differences observed two different sites in the cerebral cortex and scalp are called as "brain waves" which have characteristic waveforms and rhythms correspondently to mental and physical conditions. Brain waves are usually classified into four types, i.e. "alpha wave", "beta wave", theta wave and "delta wave" based on their frequencies. Among these, alpha wave, which usually lies in the frequency range of 8–13 hertz, strongly, extensively and continuously appears as mind and body relax. While beta wave, which usually lies in the frequency range of 18–30 hertz, strongly and extensively appears as mind and body contract. Theta and delta waves, which are 4–8 hertz or less than 4 hertz respectively, are relevant to hypnosis and sleep: It is said that theta wave strongly appears in hypnagogic stage, while delta wave in turn becomes predominant as sleep becomes deeper. As seen in Inoeu et al., *The EEG of Mental Activities*, pp.136–148 (1988), certain theta wave which is observed as predominant rhythm of 6–7 hertz around the frontal midline in adult is called as "Fm theta" and said to be closely relevant to mental tasks. One can observe Fm theta appearing around the frontal midline in persons who are in mental tasks, and its magnitude and distribution become strong and extensive as the persons' attention and concentration increase.

Since as described above Fm theta is closely connected with attention and concentration, if Fm theta is artificially induced in workers, then it is expected to improve their attention and concentration as well as to improve efficiency and accuracy of tasks. There have been however available no devices and processes which can be used to artificially induce Fm theta.

SUMMARY OF THE INVENTION

In view of the foregoing, one object of this invention is to provide an audible sound which enables artificial induction of Fm theta in human when auditorily administered.

Another object of this invention is to provide a method which enables artificial generation of such audible sound.

Further object of this invention is to provide a device which enables artificial generation of such audible sound.

Still further object of this invention is to provide a recorded medium which reproduceablly records such audible sound.

The present inventors studied various means which might solve these objects, leading to the finding that Fm theta much more strongly and extensively appeared in human when administered via the auditory sense with an audible sound containing a modulated wave where a very low-frequency wave of about 20 hertz or lower was superposed on an audio low-frequency wave. The present inventors further studied various methods and devices which might enable artificial generation of such audible sound, leading to the finding that it was easily obtainable by amplitude-modulating an audio low-frequency with a very low-frequency wave of about 20 hertz or lower, and subjecting to electroacoustic transduction the obtained electric signal which contained a modulated wave where the very low-frequency wave was superposed on the audio low-frequency wave.

Based on these novel findings, this invention provides an Fm theta-inducing audible sound which contains a modulated wave where a very low-frequency wave of about 20 hertz or lower is superposed on an audio low-frequency wave.

This invention also provides a method to generate such audible sound, which comprises amplitude-modulating an audio low-frequency with a very low-frequency wave of about 20 hertz or lower, and subjecting to electroacoustic transduction the obtained electric signal which contains a modulated wave where very low-frequency wave is superposed on the audio low-frequency wave.

Further this invention provides a device to induce Fm theta, which comprises a modulated wave-generating circuitry to generate a modulated wave where a very low-frequency wave of about 20 hertz or lower is superposed on an audio low-frequency wave, and an electroacoustic transducer to transduce said modulated wave into an audible sound, said electroacoustic transducer being connected with an output terminal of said modulated wave-generating circuitry.

Still further this invention provides a recorded medium to induce Fm theta, which bears a track of magnetically or optically recorded modulated wave where a very low-frequency wave of about 20 hertz or lower is superposed on an audio low-frequency wave, said recorded medium giving an audible sound containing said modulated wave when reproduced.

The audible sound of this invention stimulates the appearance of Fm theta in human brain waves when auditorily administered. In particular the audible sound also stimulates the appearance of alpha wave when the very low-frequency lies within the range of about 2–10 hertz.

The method and device of this invention are to artificially generate such audible sound: Amplitude modulation of an audio low-frequency wave by a very low-frequency wave of about 20 hertz or lower gives an electric signal containing a modulated wave where the very low-frequency wave is superposed on the audio low-frequency wave. Electroacoustic transduction of this electric signal gives an audible sound which contains the above mentioned modulated wave. The recorded medium of this invention gives an audible sound which contains a modulated wave where a very low-frequency wave is superposed on an audio low-frequency wave when reproduced with appropriate reproducing devices.

Figure 1:
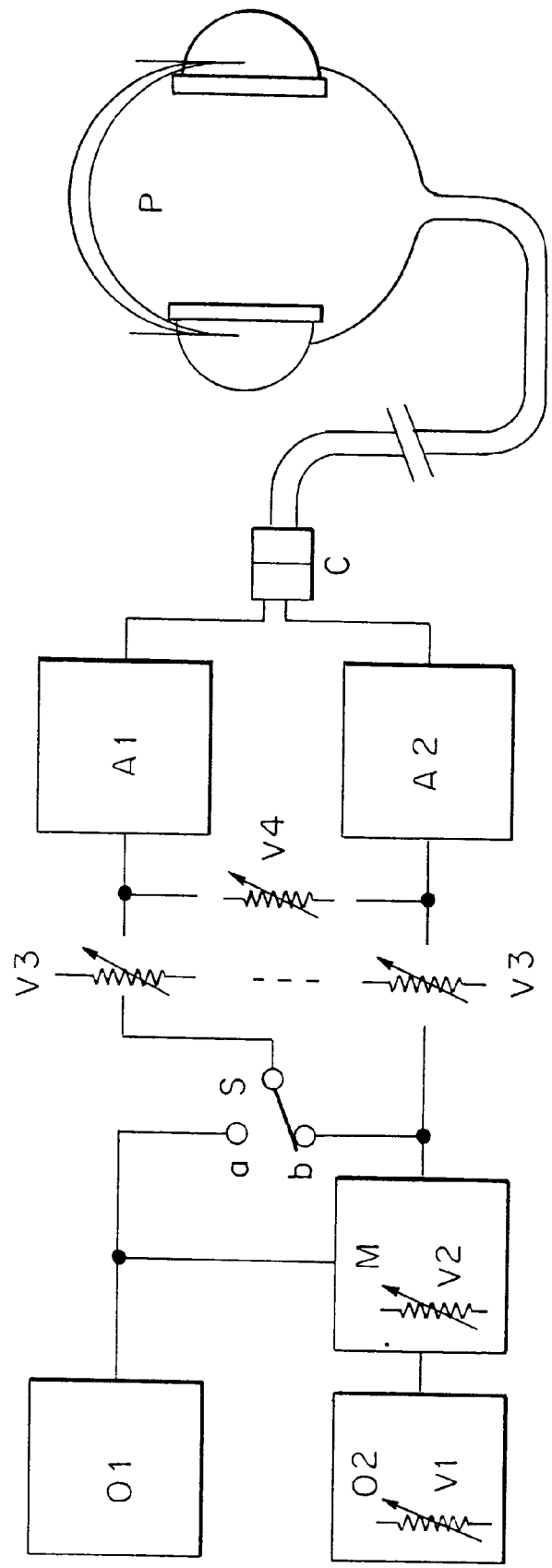
FIG. 1 is the block diagram of the electric constitutive part in an Fm theta-inducing device which generates the audible sound of this invention.

In the Figures, the symbols O1 and O2 designate oscillating circuitries; A1 and A2, amplifying circuitries; M, modulating circuitry; V1 through V4, variable resistors; S, changeover switch; C, connector; P, headphone; FSM, frequency-modulating circuitry; RFP; high-frequency power amplifying circuitry; FSR, receiving circuitry; ANT1 and ANT2, antennas; reference numeral 1, microprocessor; 2, appearing timing memory circuitry; 3, duration memory circuitry; 4, clock oscillator; 5, interface; 6, modulated wave-generating circuitry; 7, magnetic recording device; and 8, magnetic tape.

DETAILED DESCRIPTION OF THE INVENTION

Now explaining this invention in detail in conjunction with several embodiments and experiment, the wording "modulated wave" as referred to in this invention means those where a very low-frequency wave of about 20 hertz or lower is superposed on an audio low-frequency wave. Such audio low-frequency wave is feasible with continuous or pulsatile waves which have an appropriate waveform and usually a frequency exceeding that of the very low-frequency but not exceeding about 20,000 hertz. After testing various low-frequency waves using healthy volunteers, several volunteers appealed a decreased audibility and/or slight uncomfortableness when audio low-frequency waves exceeded about 6,000 hertz. Actually it is preferable to choose an audio low-frequency wave of about 50–3,000 hertz, desirably, about 100–500 hertz, much more desirably, about 120–200 hertz while considering both the frequency of the very low-frequency wave and frequency characteristics of electroacoustic transducers to be used. Similar studies on waveforms revealed that continuous waves such as sign wave and pulsatile waves, for example, saw-tooth wave, square wave, triangle wave and rectangular wave with a relatively long duration were suitable. While the very low-frequency wave is feasible with continuous or pulsatile waves of about 20 hertz or lower, usually, about 2–10 hertz which are desirably in continuous waveform such as sign form or pulsatile form with a relatively long duration as the audio low-frequency wave is.

To generate such a modulated wave, electric circuitries which are usually called as "modulated wave-generating circuitry" are feasible and such an electric circuitry comprises, for example, a first oscillating circuitry to generate an audio low-frequency wave, a second oscillating circuitry to generate a very low-frequency wave, and a modulating circuitry with an input terminal connected with output terminals of the oscillating circuitries so as to modulate the former audio low-frequency wave with the latter very low-frequency wave. More particularly an audio low-frequency wave which is generated in the first oscillating circuitry is amplitude-modulated in the modulating circuitry with a very low-frequency wave which is generated in the second oscillating circuitry, thus obtaining electric signals which contain a modulated wave where the very low-frequency wave is superposed on the audio low-frequency wave. There are no limitations in circuits and circuit elements in such oscillating and modulating circuitries as long as modulated waves appearing at an output terminal of the modulating circuitry fulfills the aforementioned requirements: Usually such circuitries are constituted mainly with transistors, field-effect transistors and/or integrated circuits. This invention does not hinder the insertion of appropriate amplifying and/or matching circuitry between modulating circuitry and electroacoustic transducer when electroacoustic transducer can not be substantially driven only with modulating circuitry as is the case that the output of modulating circuitry is too low or that the output terminal of the modulating circuitry is incompatible with electroacoustic transducer due to impedance mismatch. This invention shall of course include such embodiments and modifications.

The modulated wave thus obtained bears a waveform as such where very low-frequency wave encloses audio low-frequency wave and the magnitude of audio low-frequency wave periodically varies in accordance with the frequency of very low-frequency wave. The present inventors studied various modulated waves with different modulation degrees for both Fm theta inducibility and side effects in healthy volunteers leading to the finding that Fm theta of the highest level was induced without causing substantial side effects such as uncomfortableness when modulation degree was in the range of about 30–100%, desirably, about 60–90%. Since the most efficacious modulation degree and frequencies of audio low-frequency and very low-frequency waves usually vary dependently on particular subjects, it is desirable to provide in modulated wave-generating circuitry a function of changing their modulation degree and/or oscillating frequencies within the prescribed ranges so that particular subjects can receive an audible sound with the most appropriate modulation degree and frequencies.

By the way, Fm theta inducibility of the audible sound of this invention can be notably augmented by imparting thereto the "1/f fluctuation". Particularly it was revealed that by allowing the appearing timing, duration, frequency and/or magnitude of the auditory stimulus in accordance with the 1/f fluctuation, the audible sound and 1/f fluctuation synergetically operated and this led to an elevated Fm theta induction which was hardly attainable with either audible sound or 1/f fluctuation. More particularly series with the 1/f fluctuation which can be sampled from long-term variations in biological phenomena including brain wave, heart beat, respiration and body heat are very useful because by varying the appearing timing, duration, frequency and/or magnitude of audible sound in accordance with such a series, an extremely high level of Fm theta is induced with minimum stimuli and retained over an extended time period even after stimulation. This would be explained as follows: Series with the 1/f fluctuation, which are sampled from long-term variations in human biological phenomena, contain a number of important signals relevant to the biological regulatory mechanisms including nerve mechanism and when administered via the auditory sense, such signals very effectively act in stimulation of Fm theta induction to enhance physiological activities of the audible sound of this invention. To impart such fluctuation to the audible sound of this invention, for example, a series as described above is memorized in microcomputer and electric signals with artificial 1/f fluctuation which are led out therefrom are supplied via interface to the aforementioned oscillating and modulating circuitries.

The electric signal obtained as above is then supplied to an electroacoustic transducer where the electric signal is transduced into an audible sound which contains the modulated wave. The wording "audible sound" as referred to in this invention means sound waves which are perceivable by human auditory organ, therefore the wording "electroacoustic transducer" as referred to in the above shall mean those which transduce into a sound wave an electric signal which contains the modulated wave. Particular electroacoustic transducers are, for example, those of electromagnetic type such as electrodynamic loudspeaker and electromagnetic loudspeaker, electrostatic types such as electrostatic loudspeaker and piez-oelectric loudspeaker, and combinations thereof. There are no limitations in operation principle, shape and size of electroacoustic transducers and any transducers can be used in this invention as long as subjects can perceive via their auditory organs the modulated wave of this invention. Miniaturized headphones and earphones are however suitable when subjects use a device to generate the audible sound of this invention while carrying it.

Procedures feasible to supply to electroacoustic transducer a modulated wave which has been generated in modulated wave-generating circuitry are classified briefly into two types: One is wire type where modulated wave-generating circuitry and electroacoustic transducer are directly connected with cable or the like. With this type, subjects or assistants usually operate an electric constitutive part including modulated wave-generating circuitry at the place where the subjects actually listen to the audible sound. The other is wireless type where an electric constitutive part including modulated wave-generating circuitry and another electric constitutive part including electroaccustic transducer are separately provided and the output signal of the modulated wave-generating circuitry is supplied to the latter electric constitutive part via radio or optical communication. In such wireless type, assistants usually operate the former electric constitutive part at a remote place rather than the place where subjects actually listen to the audible sound. Although with respect to Fm theta induction there are no substantial differences between these two types, the latter wireless type has additional merits that a plurality of subjects can simultaneously listen to the audible sound with ease, as well as that they can freely move within the area where transmission arrives.

Electric signals which contain the modulated wave obtained as above can be reproduceably recorded in magnetic or optical media. When reproduced with appropriate reproducing devices, such a recorded medium gives an electric signal containing the modulated wave which can be transduced similarly as above into the audible sound of this invention. The method of this invention of course includes these embodiments. The wording "recorded medium" as referred to in the above usually means magnetic media such as magnetic tape, magnetic disk and magnetic floppy and optical medium such as optical disk and the method to record modulated wave in such a medium is arbitrarily chosen dependently on particular media. In case that medium is, for example, a magnetic tape of compact cassette type, the magnetic tape is allowed to run while keeping it in contact with magnetic head and energizing it with an electric signal containing the modulated wave. While in case that medium is, for example, a compact disk, an electric signal containing modulated wave is once converted into a digital signal, then a master disk where the digital signal is memorized in optically readable manner is made. Thereafter a disk material such as polycarbonate is press-molded using the master disk, thus a compact disk with a track of recorded modulated wave is obtained. In case that medium is either of video tape, video disk and the like which can record pictures, one can record pictures capable of inducing Fm theta and/or alpha wave in addition to the modulated wave of this invention.

Since the audible sound of this invention arises no substantial differences in induced Fm theta when subjects listen to it with one ear or both ears, both monophonic and stereophonic modes are feasible in the above described recording. However with stereophonic mode, for example, one can record both modulated and non-modulated low-frequency waves on different tracks in the same medium so that subjects are permitted to usually listen to one track which records modulated wave but, if necessary, listen to the modulated and non-modulated low-frequency waves while stereophonically reproducing and arbitrarily switching the tracks. Dependently on subjects, after listening to the audible sound of this invention over an extended time period, they may have fatigue and/or habituation to the audible sound which are however minimized by recording and reproducing as above.

The recorded medium thus obtained gives an electric signal containing the modulated wave of this invention when reproduced. There are no limitations in reproducing devices as long as such electric signal can be obtained therewith: Usually, audio and video devices for home or business use are feasible.

Now explaining the way of administering the audible sound of this invention, dependently on uses but generally, it is preferable to set the audible sound in somewhat strong level at first, then gradually in lower level. In case that administration is for improvement of attention and concentration during metal tasks, the audible sound is arbitrarily administered for appropriate time period before or during each mental task. While in case that administration is for prevention or treatment of diseases and the like, the audible sound is administered, for example, 1–7 days/week over 1 month to 1 year at a dosage of up to about 2 hours/dose at maximum 1–3 times/day while carefully monitoring subjects' conditions. The sound pressure of the audible sound at this time is usually set to about 20–90 dB, desirably, about 30–80 dB dependently on uses and subjects. The audible sound of this invention generally gives no substantial differences in Fm theta inducibility when subject listen to it with one ear or both ears. Dependently on subjects, the audible sound of this invention may stimulate the appearance of Fm theta in subjects with very short-time dose or even with no dose when they halve listened to it over an extended time period. The audible sound of this invention is useful as mental training means for such subjects.

Several Examples will be given hereinafter to illustrate Fm theta-inducing devices and recorded media which are applications of the method to generate the audible sound of this invention.

EXAMPLE 1
Fm Theta-inducing Device

FIG. 1 is a block diagram of the electric constitutive part in an Fm theta-inducing device which generates the audible sound of this invention. In FIG. 1 symbols O1 and O2 designate a first and second oscillating circuitries respectively where operation amplifiers are usually used. The first oscillating circuitry O1 is to generate a sign wave of about 150 hertz, while the second oscillating circuitry O2 is to generate a very low-frequency sign wave of about 2–10 hertz. In the second oscillating circuit O2 is provided a variable resistor V1 which is to change the frequency of the very low-frequency wave within the range of about 2–10 hertz. Symbol M designates a modulating circuitry whose input terminal is connected with output terminals of the first and second oscillating circuitries O1 and O2 so that the low-frequency and very low-frequency waves are subjected to amplitude modulation here to lead out at an output terminal of the modulating circuitry M a modulated wave where the very low-frequency wave is superposed on the low-frequency wave. A variable resistor V2 provided in the modulating circuitry M is to change the degree of amplitude modulation within the range of about 30–100%. The output terminal of the first oscillating circuitry O1 is connected via a changeover switch S to an input terminal of a first amplifying circuitry A1, while an output terminal of the modulating circuitry M is connected with an input terminal of a second amplifying circuitry A2 and a contact b in the changeover switch S. To output terminals of the first and second amplifying circuitries A1 and A2 are removably connected via a connector C a headphone P as electroacoustic transducer. Variable resistors V3 and V3 provided at the input terminals of the pair of amplifying circuitries A1 and A2 are to optimize the magnitudes of audible sounds radiated from the right- and left-channel loudspeaker units in the headphone P by changing the magnitudes of input signals for the amplifying circuitries A1 and A2. Another variable resistor V4 provided across the input terminals of the pair of amplifying circuitries A1 and A2 is to balance audible sounds radiated from the right- and left-channel loudspeaker units in the headphone P by changing the magnitudes of electric signals to be supplied to the amplifying circuitries A1 and A2.

Figure 2:
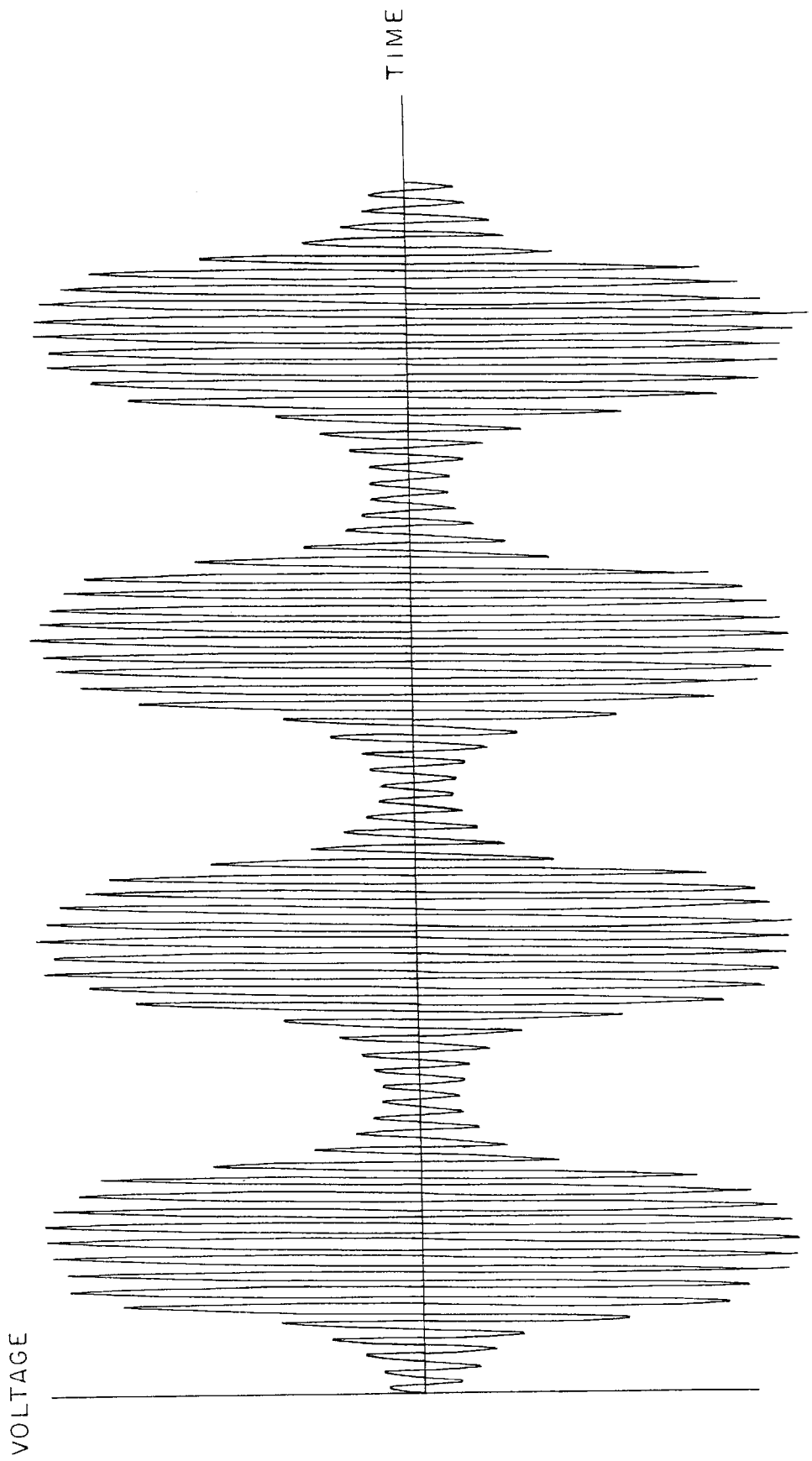
FIG. 2 illustrates the waveform of an audible sound which is given with the Fm theta-inducing recorded media in Examples 1 and 4.

Now explaining the operation of this Example, when the whole circuitries are energized while keeping the changeover switch S at the position of contact b, outputs from the first and second oscillating circuitries O1 and O2 are supplied to the modulating circuitry M. Both outputs are mixed here for amplitude modulation and a modulated wave having a waveform as shown in FIG. 2 is led out at the output terminal of the modulating circuitry M. As seen in FIG. 2, in this modulated wave a sign wave of about 2–10 hertz is superposed on another sign wave of about 150 hertz. The output of the modulating circuitry M is then amplified in the amplifying circuitries A1 and A2 to a level high enough to energize the pair of loudspeaker units in the headphone P. When the changeover switch S is turned to the position of contact a, the modulated wave is supplied only to the second amplifying circuitry A2, while the first amplifying circuitry A1 receives the low-frequency wave of about 150 hertz which has been generated by the first oscillating circuitry O1. In this case, one loudspeaker unit in the headphone P radiates an audible sound which contains the modulated wave, while the other loudspeaker unit another audible sound whichi contains non-modulated sign wave.

Since this Example is arranged in this way, when subjects operate it while putting the headphone on their head, they can listen to an audible sound which contains either a sign wave of about 150 hertz or a modulated wave where another sign wave of about 2–10 hertz is superposed on the former sign wave.

EXAMPLE 2
Fm Theta-inducing Device

Figure 3:
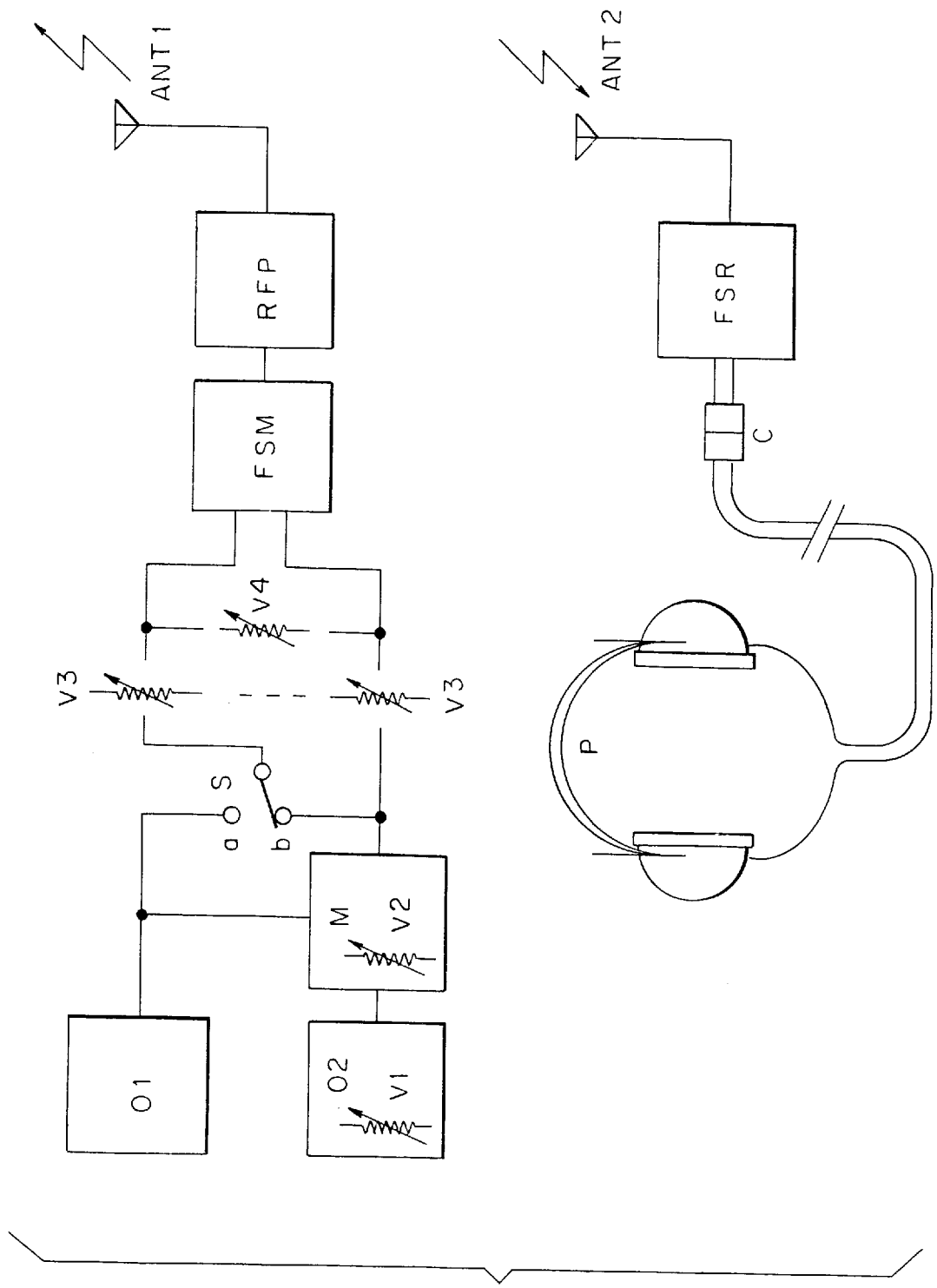
FIG. 3 is the block diagram of the electric constitutive part in an Fm theta-inducing device which generates the audible sound of this invention.

FIG. 3 is a block diagram of the electric constitutive part in another Fm theta-inducing device where outputs of a modulated wave-generating circuitry are supplied to an electroacoustic transducer in wireless manner. Symbols O1, O2, M, V1 through V4, P and C in FIG. 3 are to refer to the same circuitries or circuit elements as used in the Example shown in FIG. 1 and these circuitries and circuit elements are used with the same purpose or to achieve substantially the same functions.

As shown in FIG. 3, this Example consists of transmitting and receiving systems. In the transmitting system a modulated wave and a sign wave which have been generated in first and second oscillating circuitries O1 and O2 and a modulating circuitry M are supplied similarly as in the previous Example to an input terminal of a stereophonic frequency-modulating circuitry FSM via a changeover switch S. The frequency-modulating circuitry FSM usually comprises a low-frequency amplifying circuitry to amplify the modulated and sign waves applied to the aforementioned input terminal, and a frequency-modulating circuitry having an input terminal connected with an output terminal of the low-frequency amplifying circuitry to convert the aforementioned modulated and sign waves into frequency-modulated high-frequency waves. To an output terminal of the frequency-modulating circuitry FSM is connected an input terminal of a high-frequency power amplifying circuitry RFP to amplify the above high-frequency waves, while an output terminal of the high-frequency power amplifying circuitry RFP is connected with an antenna ANT1 which is to radiate high-frequency waves. While the receiving system comprises an antenna ANT2 to receive high-frequency waves, a stereophonic receiving circuitry FSR to decode high-frequency voltages from the antenna ANT2 into the original modulated and sign waves, and a headphone P as electroacoustic transducer to convert outputs of the receiving circuitry FSR into audible sounds.

Now explaining the operation of this Example, since this Example is arranged in this way, when the transmitting and receiving systems are simultaneously operated, respective loudspeaker units in the headphone P radiate audible sounds which contain either a sign wave of about 150 hertz or a modulated wave wherein another sign wave of about 2–10 hertz is superposed on the former sign wave.

Because of this arrangement, by providing one or more receiving systems against one transmitting system, allowing particular subjects to carry one receiving system and further allowing them to arbitrarily operate ownm receiving systems while putting on its headphone to their head, they can listen to the audible sound of this invention. This Example is suitable to allow a plurality of subjects to listen to the audible sound in a relative large space at the same time.

EXAMPLE 3
Fm Theta-inducing Recorded Medium

This Example illustrates a magnetic recorded medium which gives an audible sound whose appearing timing and duration vary in accordance with the 1/f fluctuation when reproduced.

Figure 4:
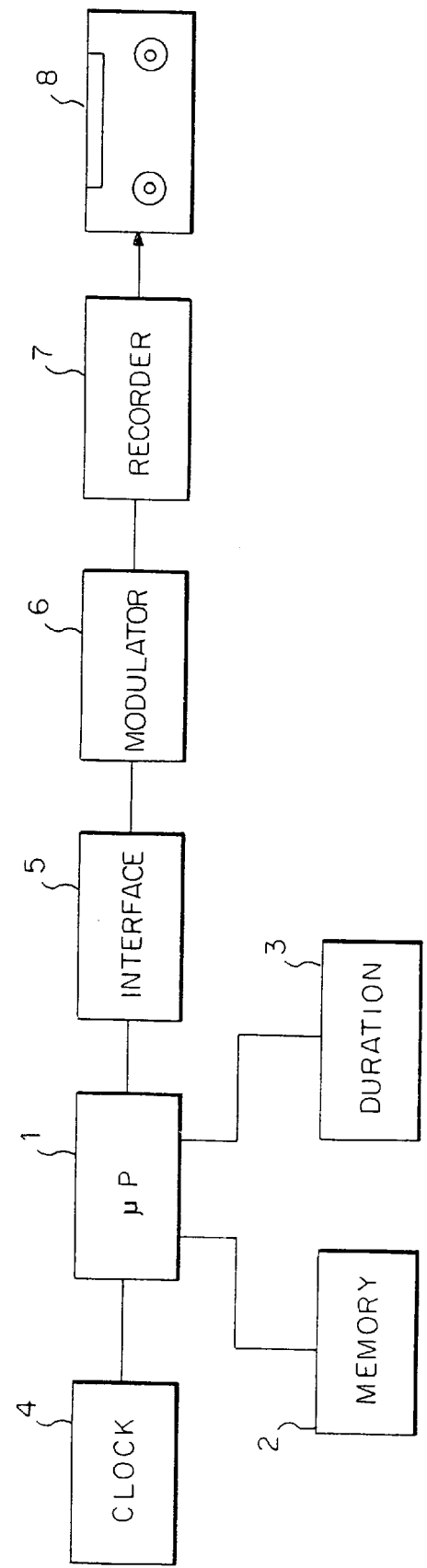
FIG. 4 is the block diagram of an electric system which is to record in a magnetic recording medium the modulated wave of this invention.

Now explaining along with FIG. 4 an electric circuitry to generate a modulated wave which gives such audible sound, in the Figure, reference numeral 1 designates a microprocessor to which an appearing timing memory circuitry 2, a duration memory circuitry 3 and a clock oscillator 4 are connected to form a microcomputer. Separately 25 types of time series with the 1/f fluctuation which have been sampled from Fm theta in 5 healthy volunteers in twenties, 3 men and 2 women, are geometrically divided into 5 steps within 0–20 times/minute for appearing timing and also into 6 steps within 0–60 seconds for duration, both of which are then memorized in the appearing timing memory circuitry 2 and duration memory circuitry 3. The microprocessor 1 is set such that it controls clock pulses to generate a series of pulses which correspond to the appearing timing and duration series. Since the microprocessor 1 has a limited memorizing capacity, it repeatedly returns to the starting data after referring to prescribed numbers of data in the appearing timing and duration series. The prescribed number of artificial irregular signals thus obtained are then processed by an interface 5 into control signals with the 1/f fluctuation for a modulated wave-generating circuitry 6. The modulated wave-generating circuitry 6 comprises a first oscillating circuitry to generate a sign wave of about 150 hertz, a second oscillating circuitry to generate a sign wave of about 8 hertz, and a modulating circuitry with an input terminal connected with output terminals of the first and second oscillating circuitries so as to modulate the former sign wave with the latter sign wave, and the control signals from the interface 5 are applied to the modulating circuit in the modulating wave-generating circuitry 6 to control its output. The output terminals of the first and second oscillating circuitries in the modulated wave-generating circuitry 6 are separately connected to different input terminals in a stereophonic magnetic recording device 7.

All the circuitries were turned on with this connection and while monitoring waveforms as appeared at the output terminal of the modulated wave-generating circuitry 6 with oscilloscope, the modulated wave was adjusted to a modulation degree of about 80% and at the same time a magnetic tape 8 of compact cassette type which had been injected in the magnetic recording device 7 was allowed to run at a rate of 4.8 cm/second, thus recording a sign wave of about 1.50 hertz and a modulated wave where another sign wave of about 8 hertz was superposed on the former sign wave on different tracks in the magnetic tape 8. The magnetic tape was of conventional type with a tape width of 3.81 m.

The recorded medium in this Example, which beared a track of magnetically recorded sign wave of about 150 hertz and another track of magnetically recorded modulated wave where another sign wage of about 8 hertz was superposed on the former sign wave, gave audible sounds which contained either the modulated wave or sign wave when reproduced. The recorded medium in this Example is reproduceable with usual reproducing devices, handleable and portable with ease and this permits workers to carry it along with a reproducing device and arbitrarily listen to the audible sound of this invention at a place where they actually do mental tasks. The audible sound from the recorded medium in this Example has an extremely high Fm theta inducibility because its appearing timing and duration are both devised to vary in accordance with the 1/f fluctuation.

Although in this Example only the appearing timing and duration of the audible sound are set variable in accordance with the 1/f fluctuation, it is also possible to vary one of them in the same way and the other in irregular way, as well as to vary in addition to the appearing timing and duration the magnitude and/or frequency in either or both of the low-frequency and very low-frequency waves within prescribed ranges in accordance with the 1/f fluctuation. This example concretely refers only to the use of series which is sampled from long-term variations in human Fm theta: The present inventors tested similarly as above other series which were sampled from long-term variations, for example, in heart beat, blood pressure, respiration, body heat and the like, leading to results which were slightly inferior but almost the same as in the case of Fm theta.

EXAMPLE 4
Fm Theta-inducing Recorded Medium

Provided were a first oscillating circuitry to generate a sign wave of about 150 hertz, a second oscillating circuitry to generate another sign wave of about 8 hertz, a modulator with amplifying circuitry and a stereophonic magnetic recording device which were connected as follows: An output terminal of the first oscillating circuitry was connected to the modulator and an output terminal in the magnetic recording device; an output terminal of the second oscillating circuitry, to an input terminal of the modulator; and an output terminal of the modulator, to a remaining input terminal in the magnetic recording device. All these circuitries were turned on and while monitoring with oscilloscope the waveform of the modulated wave as appeared at the output terminal of the modulator, the modulated wave was adjusted to a modulation degree of about 80%. Under these conditions a magnetic tape of compact cassette type which had been injected in the magnetic recording device was allowed to run at a rate of 4.8 cm/second, thus recording the modulated wave and a non-modulated low-frequency wave, i.e. the sign wave of about 150 hertz, on different tracks in the magnetic tape. The magnetic tape was of conventional type wit a tape width of 3.81 mm.

The recorded medium in this Example gave audible sounds which contained either a sign wave or a modulated wave where another sign wave of about 8 hertz was superposed on the former sign wave as shown in FIG. 2 when reproduced. The recorded medium in this Example is reproduceable with usual reproducing devices, handleable and portable with ease and this permits workers to carry it along with a reproducing device and arbitrarily listen to the audible sound of this invention at a place where they actually do mental tasks.

EXAMPLE 5
Fm Theta-inducing Recorded Medium

This Example illustrates an optical recorded medium which gives the audible sound of this invention when reproduced. In this Example a magnetic tape which magnetically recorded prescribed modulated and non-modulated low-frequency waves on different tracks was made at first, then the magnetic tape was reproduced and the outputs were optically recorded in a commercially-available writable optical disk with optical recording device.

Similarly as in Example 3, a sign wave of about 150 hertz and a modulated wave with the 1/f fluctuation from long-term variations in biological phenomena where another sign wave of about 8 hertz was superposed on the former sign wave were generated and then stereophonically recorded for 8 minutes on different tracks in a magnetic tape using magnetic recording device. The magnetic tape as used was of open-reel type with a tape width of 6.25 mm and the running rate during recording was set to 19 cm/second. Thereafter similarly as in Example 4 a sign wave of about 150 hertz and 5 varieties of modulated waves were generated and recorded on the remaining area in the magnetic tape while changing the frequency of the latter sign wave in the order of 2, 10, 4, 8, 6, 7, 4 and 10 hertz after every 10 second pause and keeping respective frequencies for 1 minute. Each modulated wave was set to a modulation degree of about 80% similarly as in Examples 3 and 4, while recording of non-modulated sign wave in the other track was suspended when generation of modulated waves was in pause.

The magnetic tape thus obtained was injected in a magnetic reproducing device and its output terminal was connected via mixer to an input terminal of conventional simplified optical recording device. Thereafter the optical recording device was injected with an 8 inch writable optical disk "CDM-V8" commercialized by Pioneer Electric Corporation, Tokyo, Japan and both devices were brought into operation to record outputs of the magnetic tape in the optical disk. The sampling frequency and quantizing bit number during the optical recording were set to 44.1 kilohertz and 16 bits respectively, while in the optical disk several subcodes were provided to address respective modulated waves in the former and latter half records.

The optical recorded medium thus obtained, which beared a track of recorded sign wave of about 150 hertz and another track of recorded modulated wave where another sign wave of 2–10 hertz was superposed on the former sign wave, gave audible sounds which contained either of these sign and modulated waves when reproduced. The recorded medium in this Example is reproduceable with usual reproducing devices, handleable and portable with ease and this permits workers to carry it along with an reproducing device and before or after mental tasks arbitrarily listen to the audible sound of this invention at a place where they actually do mental tasks. Further the recorded medium in this Example permits workers to repeatedly listen to certain modulated waves which may be most efficacious to them because in the recorded medium in this Example several subcodes are provided to address respective modulated waves.

The following Experiment will concretely explain the effects of this invention.

Experiment

Five each men and women in twenties with no psycho-neurosis were chosen as volunteers and stereophonic headphones were put on their head together with biological electrodes in accordance with the standard electrode arrangement recommended by the International Electroencephalogy Association. The biological electrodes were connected with "Model 1A97A", an electroencephalograph with data processor commercialized by NEC San-ei Instruments, Ltd., Tokyo, Japan, while the stereophonic headphones were connected with a magnetic reproducing device which had been injected with a recorded medium made similarly as in Example 4 except that the range of very low-frequency wave had been fairly extended. Thereafter the volunteers were loaded with the Kraepelin test for 15 minutes without receiving audible sound stimuli while detecting their brain waves which were then amplified and recorded in a data recorder "Model XR-710" commercialized by Teac Corporation, Tokyo, Japan. After completion of the former half test, the volunteers were given with 5 minute rest and then loaded with the Kraepelin test for additional 15 minutes while receiving audible sound stimuli. During the latter half test the brain waves in the volunteers were detected, amplified and recorded similarly as above. The sound pressure for each audible sound stimulus was set to about 70 dB on the volunteers' tympana.

Figure 5:
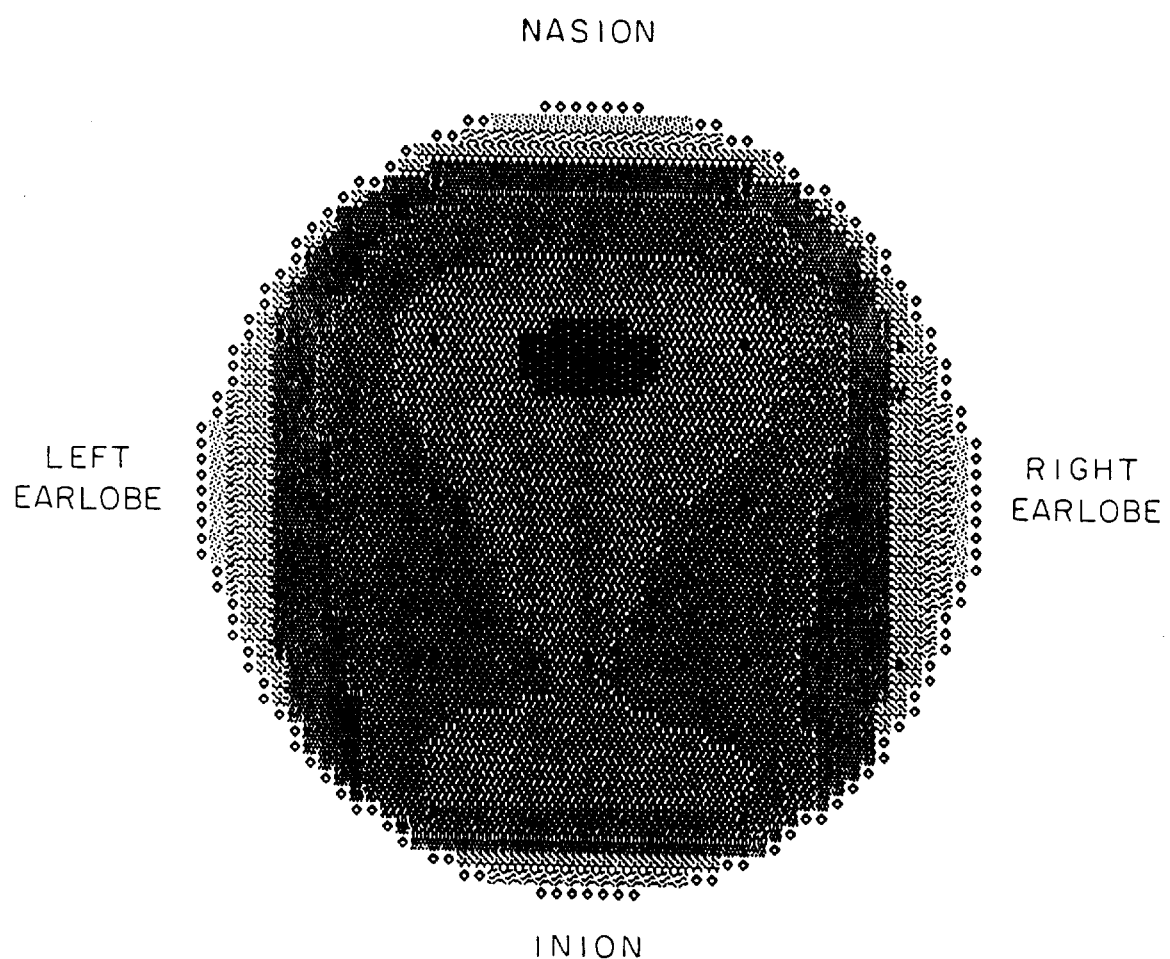
FIG. 5 is a topograph of Fm theta observed in subjects who were in mental task without listening to audible sound stimuli.
Figure 6:
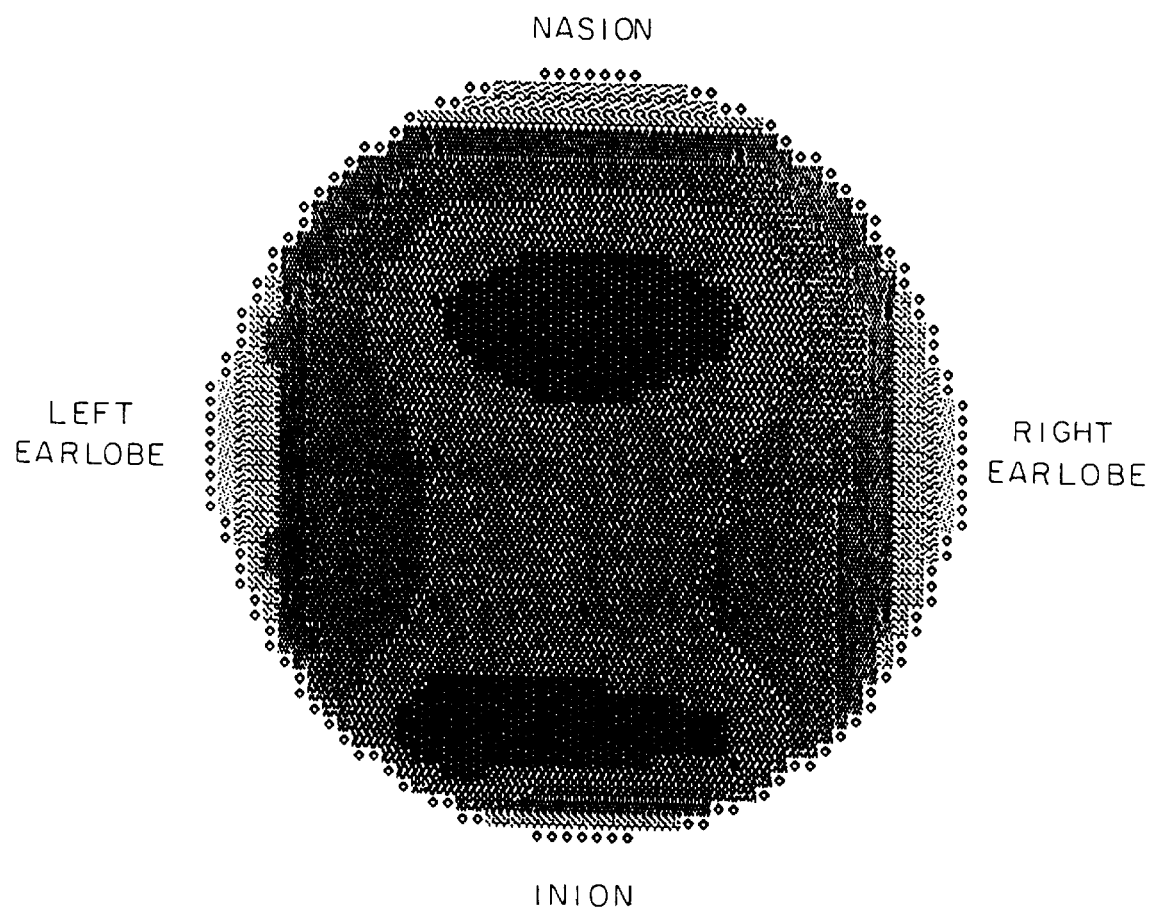
FIG. 6 is a topograph of Fm theta observed in subjects who were in mental task with listening to the audible sound of this invention.

After completion of the tests, the data in the recorder were subjected to both 9 time add calculation and frequency analysis in a signal processor "Model 7T18A" commercialized by NEC San-ei instruments, Ltd., Tokyo, Japan and the Fm theta for 10 volunteers was averaged and represented in a topograph per minute. Separately Fm theta signals which had been led out from the F3, Fz and F4 sites in the volunteers' heads for the former 15 minute and latter 15 minute mental tasks were separately calculated into averaged magnitudes (microvolts) per minute which were then put in the following equation to obtain Fm theta increasing rates (%) for respective sites. These topograph and Fm theta increasing rates were used to evaluate each audible sound for Fm theta inducibility. The results were as shown in Table 1 and FIGS. 5 and 6.

$$\text{Fm theta increasing rate (\%)} = \frac{B - A}{A} \times 100$$

As controls, there were provided another system (referred to as "Control 1" hereinafter) where volunteers received no audible sound, and one another system (referred to as "Control 2" hereinafter) where volunteers received a non-modulated wave, i.e. a sign wave of about 150 hertz, both of which were tested similarly as above.

TABLE 1

| Low-frequency wave (hertz) | Very low-frequency wave (hertz) | Fm theta increasing rate (%) F3 | Fz | F4 | Progressing rate (%) | Remarks |
|---|---|---|---|---|---|---|
| — | — | 100 | 100 | 100 | 100 | Control 1 |
| 150 | — | 100 | 101 | 101 | 100 | Control 2 |
| 150 | 2 | 108 | 115 | 111 | 113 | This invention |
| 150 | 4 | 112 | 119 | 108 | 116 | This invention |
| 150 | 6 | 121 | 130 | 119 | 128 | This invention |
| 150 | 8 | 126 | 131 | 125 | 130 | This invention |
| 150 | 10 | 120 | 125 | 117 | 123 | This invention |
| 150 | 15 | 110 | 109 | 106 | 107 | This invention |
| 150 | 20 | 105 | 106 | 103 | 105 | This invention |
| 150 | 25 | 99 | 101 | 101 | 100 | Control 3 |
| 150 | 30 | 97 | 102 | 100 | 101 | Control 4 |

As evident from the results in Table 1, although all the audible sounds commonly contained a sign wave of about 150 hertz, there were found significant differences in Fm theta increasing rates. In particular, when the very low-frequency waves were about 20 hertz or lower, the Fm theta increasing rates at all the site as tested, i.e. F3, Fz and F4, notably increased and some of them reached to about 130% of Control 1. The topographs in FIGS. 5 and 6 confirmed that Fm theta much more strongly and extensively appeared around the frontal midlines of the subjects when they were loaded with mental task while receiving the audible sound of this invention. As seen in the results for Controls 3 and 4 in Table 1, when very low-frequency waves were higher than 20 hertz, there were found no significant differences in Fm theta increasing rate against Controls 1 and 2, and some subjects appealed slight uncomfortableness and decreased concentration which were confirmed by apparent delays in progressing rates for the Kraepelin test.

With the above experimental results, it would be understood that efficacious very low-frequency waves were about 20 hertz or lower, preferably, in the range of about 2–10 hertz. Similar tests where very low-frequency wave was fixed to around 8 hertz and low-frequency wave was arbitrarily changed in the range of about 50–6,000 hertz confirmed that Fm theta increasing rate was significantly increased with low-frequency waves of about 100–500 hertz and maximized at about 120–200 hertz (data not shown). Additional tests where sign wave of about 8 hertz was superposed on another sign wave of about 150 hertz at different modulation degrees revealed that Fm theta increasing rate maximized at a modulation degree of about 30–100%. Further studies where pulsatile waves such as saw-tooth wave, square wave, triangle wave rectangular wave were replaced for sign waves confirmed that pulsatile waves with relatively long durations marked results which were slightly inferior but approximately comparable to those attained with sign waves.

Figure 7:
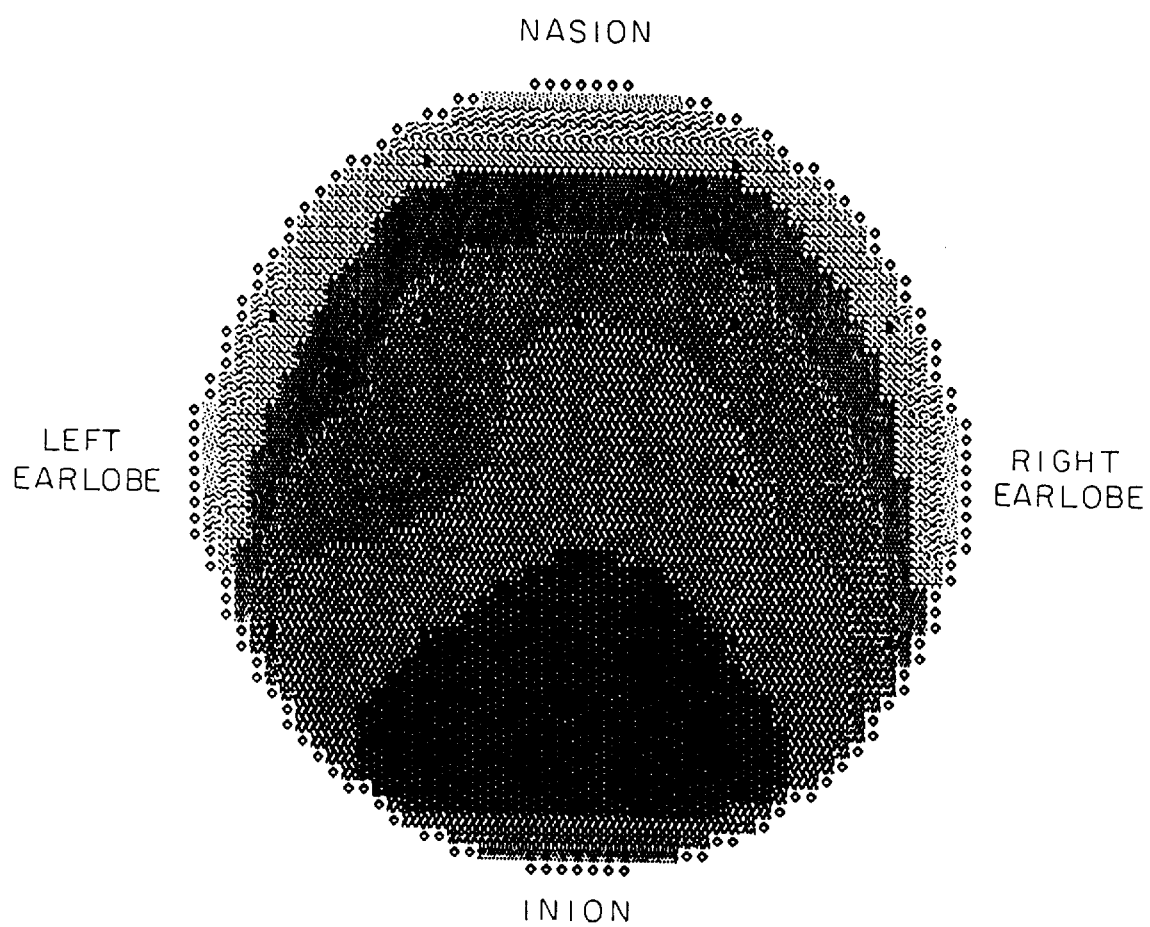
FIG. 7 is a topograph of alpha wave observed in subjects who were sitting with closed eyes without listening to audible sound stimuli.
Figure 8:
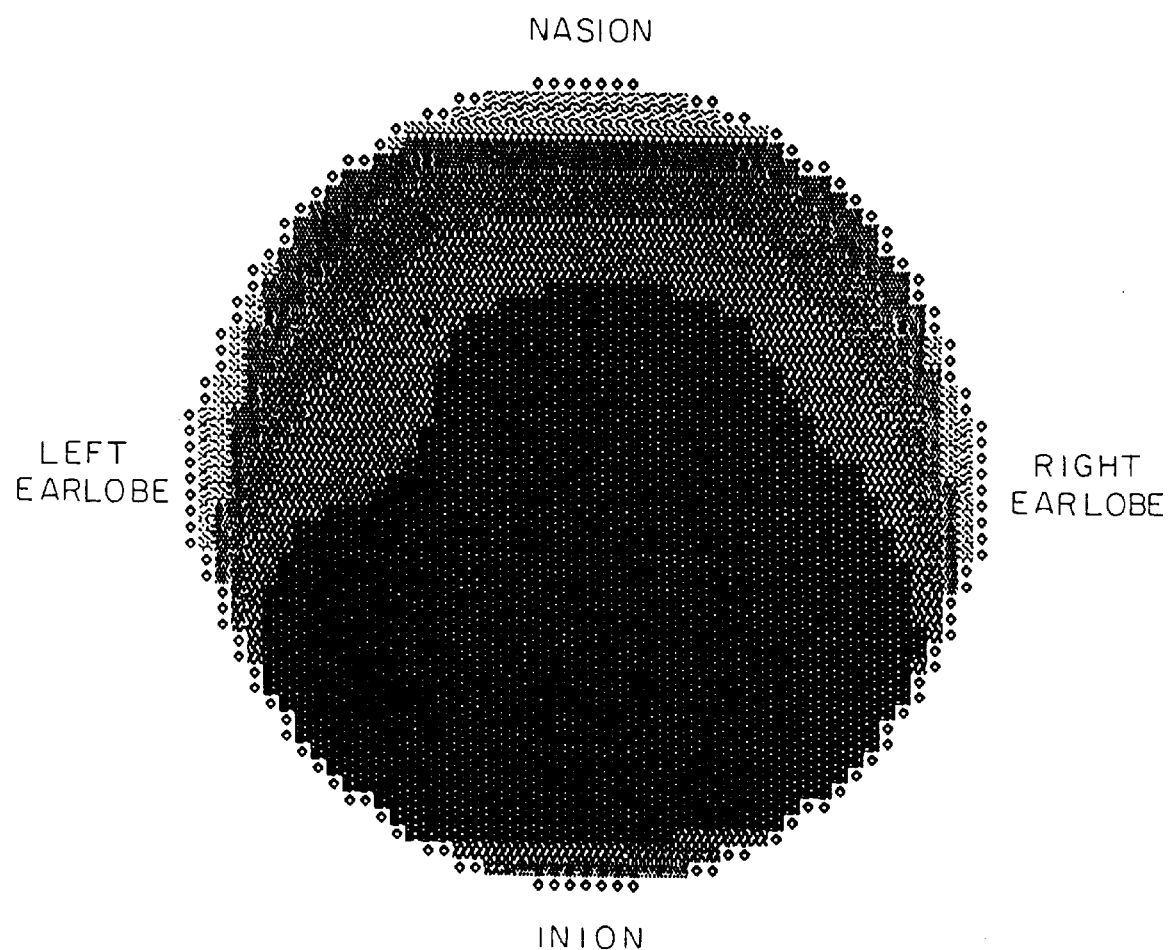
FIG. 8 is a topograph of alpha wave observed in subjects who were sitting with closed eyes with listening to the audible sound of this invention.

Separately the audible sound of this invention was further tested for effects on appearance of alpha wave using the aforementioned 10 volunteers. In particular, a stereophonic headphone was put on the head of each volunteer along with biological electrodes and the volunteers were allowed to sit and relax in chair as much as possible and then receive for 60 minutes an audible sound which contained a modulated wave where a sign wave of about 8 hertz was superposed on another sign wave of about 150 hertz. During the stimulation the brain waves in the volunteers were detected, amplified and recorded in recorder in usual manner. After completion of the test, the recorded data were subjected to frequency analysis and the alpha wave of 8–10 hertz as detected for 20 minutes immediately after starting the test was represented in topographs per minute at 5 minute intervals. After a lapse of 3 days, the volunteers received the same test except that audible sound was neglected. As the result, the audible sound of this invention led to notable changes in the subjects' alpha waves: The alpha wave without audible sound was as shown in FIG. 7, while as seen in FIG. 8 the alpha wave became stronger and much more extensive around the parietal sites in the subjects 15 minutes after starting administration of the audible sound. At the same time the appearance of beta wave was found to be notably suppressed. These tendencies were not substantially changed even when the very low-frequency wave was changed within the range of about 2–10 hertz.

These evidences suggest that the audible sound of this invention would have properties of suppressing the appearance of beta wave and also stimulating the appearance of alpha wave, as well as of stimulating the appearance of Fm theta. Since as described above alpha and beta waves are relevant to mental and physical relaxation and contraction respectively, the audible sound of this invention improves attention and concentration in subjects when they listen to it with opened eyes, while the audible sound relaxes their mind and body when they listen to it with closed eyes.

As described above, Fm theta is a good criterion for attention and concentration, therefore the results in this Experiment suggest that when used in mental tasks in general, the audible sound of this invention would improve the users' attention and concentration and keep their efficiency and accuracy during the tasks in an elevated level. The progressing rates (%) for the Kraepelin test also confirmed this: As seen in Table 1, the progressing rates (%) during task were significantly enhanced when the volunteers were loaded with it while listening to the audible sound of this invention.

The audible sound of this invention stimulates the appearance of Fm theta in subjects' brain waves when they listen to it. The audible sound also stimulates the appearance of alpha wave when the very low-frequency wave lies in the range of about 2–10 hertz. Thus the audible sound of this invention improves and stimulates in subjects desirable states in their mind and body, i.e. attention, concentration and relaxation, to which Fm theta and alpha wave are relevant when they listen to it.

Because of these, the audible sound of this invention is effective in relaxation of mind and body, improvement of creativity and efficiency in studies and relief or elimination of reduction in thinking power, concentration, working motivation, insomnia, fatigue, obsession, phobia and uncompleteness, for example, due to mental diseases such as neurosis, psychasthenia, psychosomatic disease, manic-depressive psychosis and chronic alcohol dependence and stresses including technostresses which are caused by electromagnetic waves from television set, video display, OA instrument and igniter for automobiles, in addition to improvement of attention and concentration. Thus the audible sound of this invention is useful as means to improve efficiency, accuracy, learning ability, researching ability and creativity in mental tasks and also to improve concentration during playing sports at home, working place, stadium, school, "gakushu-juku (a school for private tutoring after regular school hours)", training place, research institution and atorie, as well as means to prevent and treat a variety of mental diseases at working place, clinic, hospital and sanatorium. Dependently on subjects, the audible sound of this invention may stimulate the appearance of Fm theta with very short-term dose or even with no dose when subjects have listened to it over an extended time period. The audible sound of this invention is useful as mental training means for such subjects. Further the audible sound, which is useful as described above, is artificially and readily obtainable by the method of this invention.

The audible sound, which is very useful as described above, is easily obtainable by the method, device and recorded medium of this invention.

As described above, this invention would be greatly contributive to the art and very significant.

We claim:

1. A method to generate Fm theta-inducing audible sound which contains a modulated wave where a very low-frequency wave of about 20 hertz or lower is superposed on an audio frequency wave, which comprises:

generating the audio frequency wave with a modulated wave-generating circuitry;

generating the very low-frequency wave with the modulated wave-generating circuitry;

amplitude-modulating the audio frequency wave with the very low-frequency wave in the modulated wave-generating circuitry, to obtain a modulated wave where the very low-frequency wave is superposed on the audio frequency wave, and subjecting the modulated wave to electroacoustic transduction.

2. The method of claim 1, wherein the frequency of said audio frequency wave lies within the range of about 120–200 hertz.

3. The method of claim 1, wherein the frequency of said very low-frequency wave lies within the range of about 2–10 hertz.

4. The method of claim 1, wherein the modulation degree of said modulated wave lies within the range of about 30–100%.

5. The method of claim 1, wherein one of frequency, appearing timing, duration and magnitude of said audible sound varies in accordance with a 1/f fluctuation.

6. The method of claim 1, wherein said audio frequency wave and very low-frequency wave are in sine wave-form.

7. A device to generate Fm theta-inducing audible sound, comprising:

a modulated wave-generating circuitry to generate a modulated wave where a very low-frequency wave of about 20 hertz or lower is superposed on an audio low-frequency wave; and an electroacoustic transducer to transduce said modulated wave into the audible sound, said electroacoustic transducer being connected with an output terminal of said modulated wave-generating circuitry.

8. A device to generate Fm theta-inducing audible sound, comprising:
- a modulated wave-generating circuitry to generate a modulated wave where a very low-frequency wave of about 20 hertz or lower is superposed on an audio frequency wave; and
- an electroacoustic transducer to transduce said modulated wave into the audible sound, said electroacoustic transducer being connected with an output terminal of said modulated wave-generating circuitry;
- wherein said modulated wave-generating circuitry comprises:
- a first oscillating circuitry to generate the audio frequency wave;
- a second oscillating circuitry to generate the very low-frequency wave of about 20 hertz or lower; and
- a modulating circuitry to modulate said audio frequency wave with said very low-frequency wave, said modulating circuitry having an input terminal connected with output terminals of said first and second oscillating circuitries.

9. The device of claim 5, wherein the frequency of said audio frequency wave lies within the range of about 120–200 hertz.

10. The device of claim 5, wherein the frequency of said very low-frequency wave lies within the range of about 2–10 hertz.

11. A device to generate Fm theta-inducing audible sound, comprising:
- a modulated wave-generating circuitry to generate a modulated wave where a very low-frequency wave of about 20 hertz or lower is superposed on an audio frequency wave; and
- an electroacoustic transducer to transduce said modulated wave into the audible sound, said electroacoustic transducer being connected with an output terminal of said modulated wave-generating circuitry;
- wherein the modulation degree of said modulated wave lies within the range of about 30–100%.

12. The device of claim 5, wherein one of frequency, appearing timing, duration and magnitude of said audible sound varies in accordance with a 1/f fluctuation.

13. A therapeutic system to induce Fm theta, comprising:
- a recording medium bearing a track of magnetically or optically recorded modulated wave where a very low-frequency wave of 20 hertz or lower is superposed on an audio low-frequency wave; and
- means for playing back sound from said recording medium.

14. The system of claim 10, wherein the frequency of said audio frequency wave lies within the range of about 120–200 hertz.

15. The system of claim 10, wherein the frequency of said very low-frequency wave lies within the range of about 2–10 hertz.

16. A therapeutic system to induce Fm theta, comprising:
- a recording medium bearing a track of magnetically or optically recorded modulated wave where a very low-frequency wave of 20 hertz or lower is superposed on an audio frequency wave; and
- means for slaying back sound from said recording medium;
- wherein a modulation degree of said modulated wave lies within a range of about 30–100%.

17. The system of claim 10, wherein one of frequency, appearing timing, duration and magnitude of said audible sound varies in accordance with a 1/f fluctuation.

18. The system of claim 10, wherein said low-frequency and very low-frequency waves are in sine wave-form.

19. The system of claim 10, which is a magnetic tape or optical disk.

20. A method of increasing an amplitude of a brain wave in a subject person, the brain wave having a baseline frequency and exhibiting 1/f noise at the baseline frequency; the method comprising:
- recording a 1/f noise sample of the 1/f noise at the baseline frequency in a sample person;
- generating an unmodulated stimulus from a high-frequency stimulus;
- modulating the stimulus at the baseline frequency;
- fluctuating the stimulus according to the 1/f noise sample; and
- exposing the subject person to the modulated stimulus.

* * * * *